United States Patent [19]
Midha et al.

[11] Patent Number: 5,911,979
[45] Date of Patent: Jun. 15, 1999

[54] AQUEOUS HAIR SETTING COMPOSITION CONTAINING SILICONE GRAFTED COPOLYMER

[75] Inventors: Sanjeev Midha, Blue Ash; Peter Marte Torgerson, Washington Court House, both of Ohio

[73] Assignee: The Procter & Gamble Company, Cincinnati, Ohio

[21] Appl. No.: 08/807,845

[22] Filed: Feb. 26, 1997

Related U.S. Application Data

[63] Continuation of application No. 08/370,147, Jan. 9, 1995, abandoned.

[51] Int. Cl.$^6$ ............................................. A61K 7/06
[52] U.S. Cl. .............. 424/70.12; 424/401; 424/70.122; 424/DIG. 1; 424/DIG. 2
[58] Field of Search .................... 424/70.11, 70.12, 424/70.122, 401, DIG. 1, DIG. 2

[56] References Cited

U.S. PATENT DOCUMENTS

| | | | |
|---|---|---|---|
| 3,208,911 | 9/1965 | Oppliger | 167/87 |
| 3,957,970 | 5/1976 | Korkis | 424/70 |
| 4,030,512 | 6/1977 | Papantoniou et al. | 132/7 |
| 4,136,250 | 1/1979 | Mueller et al. | 528/29 |
| 4,185,087 | 1/1980 | Morlino | 424/70 |
| 4,277,595 | 7/1981 | Deichert et al. | 528/26 |
| 4,479,893 | 10/1984 | Hirota et al. | 252/542 |
| 4,563,347 | 1/1986 | Starch | 424/70 |
| 4,601,902 | 7/1986 | Fridd et al. | 424/70 |
| 4,654,161 | 3/1987 | Kollmeier et al. | 252/174.15 |
| 4,659,777 | 4/1987 | Riffle et al. | 525/100 |
| 4,663,413 | 5/1987 | Ward et al. | 528/26 |
| 4,689,383 | 8/1987 | Riffle et al. | 528/12 |
| 4,693,935 | 9/1987 | Mazurek | 428/352 |
| 4,724,851 | 2/1988 | Cornwall et al. | 132/7 |
| 4,728,571 | 3/1988 | Clemens et al. | 428/352 |
| 4,733,677 | 3/1988 | Gee et al. | 132/7 |
| 4,744,978 | 5/1988 | Homan et al. | 424/70 |
| 4,814,402 | 3/1989 | Nakashima et al. | 526/245 |
| 4,902,499 | 2/1990 | Bolich, Jr. et al. | 424/70 |
| 4,963,348 | 10/1990 | Bolich, Jr. et al. | 424/47 |
| 4,963,595 | 10/1990 | Ward et al. | 525/415 |
| 4,972,037 | 11/1990 | Garbe et al. | 526/245 |
| 4,981,902 | 1/1991 | Mitra et al. | 524/547 |
| 4,981,903 | 1/1991 | Garbe et al. | 524/547 |
| 4,988,506 | 1/1991 | Mitra et al. | 424/81 |
| 5,021,477 | 6/1991 | Garbe et al. | 424/70 |
| 5,061,481 | 10/1991 | Suzuki et al. | 424/63 |
| 5,100,657 | 3/1992 | Ansher-Jackson | 424/70.1 |
| 5,100,658 | 3/1992 | Bolich, Jr. et al. | 424/70.1 |
| 5,104,646 | 4/1992 | Bolich, Jr. et al. | 424/70.1 |
| 5,106,609 | 4/1992 | Bolich, Jr. et al. | 424/70.1 |
| 5,120,531 | 6/1992 | Wells et al. | 424/70.1 |
| 5,120,532 | 6/1992 | Wells et al. | 424/70.1 |
| 5,166,276 | 11/1992 | Hayama et al. | 525/329 |
| 5,219,560 | 6/1993 | Suzuki et al. | 424/63 |
| 5,229,435 | 7/1993 | Sakai et al. | 523/105 |
| 5,468,477 | 11/1995 | Kumar et al. | 424/63 |
| 5,565,193 | 10/1996 | Midha et al. | 424/70.12 |
| 5,665,337 | 9/1997 | Carballada et al. | 424/70.12 |
| 5,667,771 | 9/1997 | Carballada et al. | 424/70.12 |
| 5,753,216 | 5/1998 | Leitch et al. | 424/70.12 |
| 5,811,109 | 9/1998 | Cooper et al. | 424/401 |

FOREIGN PATENT DOCUMENTS

| | | | |
|---|---|---|---|
| 0 117 360 | 12/1983 | European Pat. Off. | A61K 7/06 |
| 0 282 720 A2 | 2/1987 | European Pat. Off. | C08G 77/38 |
| 0 408 311 A2 | 7/1990 | European Pat. Off. | C08F 230/08 |
| 0 412 704 A2 | 7/1990 | European Pat. Off. | A61K 7/06 |
| 0 412 707 A1 | 2/1991 | European Pat. Off. | A61K 7/06 |
| 5 6092-811 | 7/1981 | Japan | A61K 07/11 |
| 5 6129-300 | 10/1981 | Japan | A61K 07/06 |
| 4-359912 | 6/1991 | Japan | C08F 299/08 |
| 4-359913 | 6/1991 | Japan | C08F 299/08 |
| 4-360812 | 6/1991 | Japan | A61K 7/00 |
| 4359913 | 12/1992 | Japan . | |
| 4359914 | 12/1992 | Japan . | |
| 4360812 | 12/1992 | Japan | A61K 7/075 |
| WO 88/05060 | 7/1988 | WIPO | C08F 30/08 |
| WO 92/00303 | 1/1992 | WIPO | C07F 7/08 |

*Primary Examiner*—Robert H. Harrison
*Attorney, Agent, or Firm*—Leonard W. Lewis; Stephen T. Murphy; Tara M. Rosnell

[57] ABSTRACT

An aqueous hair setting composition, comprising: (a) from about 0.1% to about 15%, by weight, of a cationic, water soluble polymeric hair setting agent, said hair setting agent being a silicone macromer-grafted copolymer derived by polymerization of: (i) from about 1% to about 20%, by weight, silicone macromers; (ii) from about 5% to about 75%, by weight, nonionic, quaternizable monomers; and (iii) from about 5% to about 90%, by weight, nonionic, water soluble, non-quaternizable monomers; wherein at least about 5 wt/%, of the monomers, calculated by total weight of the copolymer, are quaternized and said copolymer has a backbone having a Tg of from about 30° C. to about 140° C.; and (b) from about 75% to about 99.9%, by weight, water.

12 Claims, No Drawings

AQUEOUS HAIR SETTING COMPOSITION CONTAINING SILICONE GRAFTED COPOLYMER

This is a continuation of application Ser. No. 08/370,147, filed on Jan. 9, 1995, now abandoned.

TECHNICAL FIELD

The present invention relates to aqueous hair setting compositions containing silicone grafted copolymers.

BACKGROUND OF THE INVENTION

It is widely desired to have the hair retain a particular design or style. There are many types of compositions for topical application to the hair that are designed to achieve this benefit. These include mousses, gels, lotions, hairsprays (aerosol and nonaerosol), hair rinses, and shampoos. Hair setting compositions may have many different types of ingredients, but generally have at least one type of ingredient in common—a polymeric adhesive hair setting agent.

Conventionally, hair setting compositions utilize organic polymers as hair setting agents such as octylacrylamide/acrylates/butylaminoethyl methacrylate copolymer and the ester of methylvinylether/maleic anhydride copolymer. Although these polymers can provide good hair hold properties, they have the unfortunate additional effect of leaving the hair with a relatively stiff, brittle feel.

More recently, it has become known to utilize silicone grafted copolymers as hair styling agents. These polymers contain silicone macromers attached to the backbone of the polymer, which improve hair feel versus the conventional hair setting agents. More specifically, the hair feels softer to the touch and can more easily be combed subsequent to use of the hair styling product relative to conventional hair styling polymers. Silicone grafted polymers suitable for hair care compositions are disclosed, for example in U.S. Pat. No. 5,061,481, Suzuki et al., issued Oct. 29, 1991, U.S. Pat. No. 5,219,560, Suzuki et al., issued Jun. 15, 1993, U.S. Pat. No. 5,166,276, Hayama et al., issued Nov. 24, 1992, U.S. Pat. No. 5,106,609, Bolich et al., issued Apr. 21, 1992, U.S. Pat. No. 5,100,658, Bolich et al., issued Mar. 31, 1992, U.S. Pat. No. 5,100,657, Ansher-Jackson et al., issued Mar. 31, 1992, U.S. Pat. No. 5,104,646, Bolich et al., issued Apr. 14, 1992, EPO 0 412 707, Torgerson et al., granted Feb. 4, 1994, EPO 0 412 704, Bolich et al., published Feb. 13, 1991, EPO application 92918969.4, Peffly, filed Aug. 18, 1992, EPO Application 92918839.9, Hozshuh, et al., filed Aug. 18, 1992, and EPO Application 92919224.3, filed Aug. 18, 1992.

The most commonly used forms of hair setting compositions are the various forms of spray products such as hairsprays, mousses, and other spray products.

Hair styling products typically have ethanol, water, or ethanol/water carriers for the polymeric hair setting agent. It has increasingly become desirable to market products, however, that are characterized by aqueous carriers, with little or no ethanol or other volatile organic carriers. Unfortunately, it is difficult to formulate silicone grafted copolymers that have good hair hold properties and low stickiness into aqueous vehicles without the use of volatile organic solvents, such as ethanol, cyclomethicone, or others. In general, this is because the silicone portion of the polymer is so highly hydrophobic, and therefore not soluble in water, that the polymer as a whole no longer remains soluble in water. Cationic silicone grafted copolymers which appear to be water soluble have been specifically disclosed. In JP 04360812-A, published Dec. 14, 1992, Kao Corp., JP 04359913-A, published Dec. 14, 1992, Kao corp. and JP 04359914-A, published Dec. 14, 1992, Kao Corp., for example, it is disclosed to utilize silicone grafted copolymers containing cationic monomers. Although the polymers of these references may be water soluble, they would also tend to be relatively sticky and hygroscopic, due to cationic monomer. U.S. Pat. No. 5,166,276, Hayama et al., issued Nov. 24, 1992, and EPO applications EPO application 92918969.4, Peffly, filed Aug. 18, 1992, EPO Application 92918839.9, Hozshuh, et al., filed Aug. 18, 1992, and EPO Application 92919224.3, filed Aug. 18, 1992 disclose cationic silicone grafted copolymers for use in hair care, but do not specifically discloses polymers that would have good hair hold performance, have soft feel, and be soluble in water without the aid of volatile organic solvents.

It is an object of this invention to provide aqueous hair setting compositions containing silicone grafted polymers as hair setting agents, for improved hair feel, which are not sticky and do not require the presence of volatile organic compounds to aid in solubilization of the polymer. It is a particular object of this invention to provide aqueous hair mousse compositions containing silicone grafted polymers as hair setting agents for improved hair feel, which are not sticky and do not require the presence of volatile organic compounds to aid in solubilization of the polymer.

These and other objects and benefits as may be discussed or apparent may be obtained with the present invention, which is described below.

All percentages herein are by weight of the compositions unless otherwise indicated. All ratios are weight ratios unless otherwise indicated. All percentages, ratios, and levels of ingredients referred to herein are based on the actual amount of the ingredient, and do not include solvents, fillers, or other materials with which the ingredient may be combined as commercially available products, unless otherwise indicated.

The invention hereof can comprise, consist of, or consist essentially of the essential elements described herein as well as any of the preferred or optional ingredients also described herein.

SUMMARY OF THE INVENTION

It has now been found that aqueous hair setting compositions containing water soluble silicone-grafted copolymers as hair setting agents that are essentially free of volatile organic solvents can be provided by utilizing a quaternized, silicone-grafted copolymer comprising a sufficient amount of silicone macromer to provide improved hair feel versus non-silicone macromer-containing polymers. The polymers hereof are derived by polymerization of a mixture of nonionic quaternizable monomers with nonionic, water soluble, non-quaternizable monomers, and generally, also with silicone macromers, wherein a sufficient portion of the quaternizable monomers are quaternized in the polymer subsequent to polymerization such that the polymer is soluble in water.

In particular, the present invention provides an aqueous hair setting composition, comprising:

(a) from about 0.1% to about 15%, by weight, of a cationic, water soluble polymeric hair setting agent, said hair setting agent being a silicone macromer-grafted copolymer derived by polymerization of:
  (i) from about 1% to about 20%, by weight, silicone macromer;
  (ii) from about 5% to about 75%, by weight, nonionic, quaternizable monomers; and (iii) from about 5% to about 90%, by weight, nonionic, water soluble, non-quaternizable monomers;

wherein at least about 5 wt. %, of the monomers, calculated by total weight of the copolymer, are quaternized and said copolymer has a backbone having a Tg of from about 30° C. to about 140° C.; and (b) from about 75% to about 99.9%, by weight, water

DETAILED DESCRIPTION OF THE INVENTION

Silicone Grafted Copolymer

The compositions hereof comprise from about 0.1% to about 15%, by weight, of a cationic, water soluble, polymeric hair setting agent, preferably from about 0.5% to about 10%, more preferably from about 1% to about 8%. The hair setting agent is a silicone-grafted copolymer (including mixtures of such copolymers), comprising silicone covalently bonded to the polymer backbone (i.e. silicone chains are grafted to the backbone), and are derived by polymerization of a combination of nonionic, nonquaternizable, water soluble monomers and nonionic, quaternizable monomers. The silicone macromers will generally be incorporated into the polymeric hair setting agent by conducting the polymerization of the above two types of monomers also in the presence of silicone macromer—i.e., silicone containing monomers. At least a portion of the quaternizable, monomers are quaternized. Quaternization is conducted subsequent to polymerization, and is conducted to a sufficient degree such that the polymer is soluble in water.

By "soluble in water" or "water soluble", what is meant is that the material is soluble in 25° C. deionized water at a concentration of 1.0%, preferably at 2%, more preferably at least about 10%, most preferably at about 15%. Solubility will generally, though not necessarily, be no more than about 30%. By "soluble" in reference to polymers in the compositions hereof, what is meant is that a clear or translucent solution can be formed, without the presence of solvents other than water to impart such solubility. With regard to the silicone grafted copolymers hereof, aqueous solutions thereof may be translucent, rather than clear, due to the presence of the silicone macromer grafts which are not soluble in water. However, the polymeric non-silicone backbones of the polymers hereof are of sufficient water solubility such that the polymer as a whole remains in clear or translucent solution. By "water soluble" in regard to monomers discussed herein, what is meant is that a homopolymer of the monomer having a number average molecular weight of 10,000 would be soluble in water The copolymers hereof can have any number average molecular weight of any level that is useful for providing hair setting benefits. Generally the number average molecular weight will be at least about 10,000, typically at least about 30,000, preferably at least about 50,000. Generally, though not necessarily, the molecular weight will be less than about 1,000,000, preferably less than 750,000.

The silicone macromer-grafted copolymers hereof will have a polymeric backbone with a Tg of from about 30° C. to about 140° C., preferably from about 40° C. to about 120° C., more preferably from about 40° C. to about 100° C. The silicone macromer-containing copolymers have an organic polymeric backbone, preferably a vinyl backbone or other carbon-based backbone derived from ethylenically unsaturated polymerizable monomers.

The polymers hereof are derived by polymerization of: from about 1% to about 20%, by weight, of silicone macromers, preferably from about 2% to about 15%, more preferably from about 5% to about 10%; from about 5% to about 75%, by weight, of nonionic, quaternizable monomers, preferably from about 5% to about 60%, more preferably from about 5% to about 40%; and from about 5% to about 90%, by weight, of nonionic, water soluble, non-quaternizable monomers, preferably from about 25% to about 70%, more preferably from about 30% to about 60%. The polymers hereof will also comprise monomer units in the same ranges set forth above.

At least about 5 wt. % of the monomers, by weight of the copolymer, preferably from about 5% to about 75%, more preferably from about 5% to about 60%, most preferably from about 5% to about 40%, is quaternized.

Once quaternized, the quaternizable monomers hereof substantially enhance water solubility of the silicone macromer-grafted copolymer. In quaternized form, these monomers tend to be hygroscopic (i.e., they absorb water from the atmosphere) and reduce the Tg the polymers they are incorporated into, which can result in an undesireably sticky product. The nonionic, water soluble, nonquaternizable monomers also aid in solubility of the polymer, although since they are not generally polar as the quaternized monomers hereof, they have not been found to form water soluble silicone macromer-grafter copolymers. These monomers, however, tend to absorb less water from the atmosphere than the quaternized monomers, when incorporated into the final copolymer, thus they aid in reducing stickiness of the polymer, while allowing the silicone macromer grafted polymer to remain water soluble.

When making the silicone macromer-grafted copolymer the polymerization is conducted with the quaternizable monomers in nonionic, un-quaternized form. This has been found to better facilitate random polymerization of the monomers, selection of suitable reaction solvents in which the silicone monomer-grafted monomers, (i.e., to obtain solvents in which the quaternizable monomers, and the nonquaternizable monomers are all soluble) and to provide improved polymers and hair setting products.

The quaternizable nonionic monomers hereof include quaternizable, amino-functional ethylenically unsaturated monomers, such as the amino functional derivatives of styrene, acrylamides, methacrylamides, (meth)acrylate such as the $C_1$–$C_5$ alkyl esters of acrylic acid and methacrylic acid. Preferred are $C_1$–$C_5$ alkyl amines especially $C_1$–$C_3$ amines. It is preferred to use the tertiary amines. (e.g., trialkyl amines), though it is not meant to necessarily exclude monoalkyl amines, dialkyl amines, and other alkyl amine derivatives. Especially preferred are dimethyl amino $C_1$–$C_3$ alkyl amines.

Examples of such monomers include: (i) p-dimethylaminomethyl styrene, p-dimethylamionoethyl styrene; (ii) dimethylaminomethyl acrylamide, dimethylaminopropyl acrylamide, dimethylaminopropyl methacrylamide, dimethylaminomethyl methacrylamide; dimethylaminoethyl (meth)acrylate, diethylaminoethyl (meth)acrylate, dimethylaminopropyl (meth)acrylate, and dimethylaminopropyl (meth)acrylamide.

The term "copolymer" means any polymers comprising two or more types of monomers. As will be apparent to those skilled in the art, the copolymers hereof will generally contain at least three types of monomers (i.e., "terpolymers"), or more. The three monomer types include the nonionic quaternizable monomers, the nonionic non-quaternizable monomers, and silicone macromers.

Quaternization of the amino groups can be achieved by any suitable means known in the art. These include: (1) modification with an acid such as hydrochloric acid, or lactic acid, (2) modification with a halogenated alkyl, such as methyl chloride, ethyl chloride, methyl bromide, or ethyl iodide, (3) modification with a halogenated fatty acid ester such as ethyl monochloroacetate, or methyl monochloropropionate, and (4) modification with a dialkyl sulfate such as dimethyl sulfate, or diethyl sulfate.

The use of the notation "(meth)" preceding a chemical name, such as acrylate or acrylamide, in this specification is meant to denote that methylated as well as the non-methylated versions of such species are disclosed.

The polymers of the present invention also include nonionic, nonquaternizable, water soluble monomers. Examples of such monomers include acrylamides, methacrylamides, cinamides, vinyl alcohols, vinyl pyrrolidones, vinyl oxazolidones, and (meth)acrylates, and derivatives thereof. Specific examples include acrylamide, methacrylamide, mono- and di-$C_1$–$C_6$, preferably alkyl (meth)acrylamides, such as dimethylacrylamide, dimethylmethacrylamide, isopropylacrylamide, t-butylacrylamide and isopropylmethacrylamide, diacetone acrylamide, diacetone methacrylamide, acrylylglycinamide, methacrylylglycinamide, vinyl alcohol, vinyl pyrrolidone, vinyl oxazolidone, vinylmethyloxazolidone, and poly (ethylene glycol) phenyl ether (meth)acrylate (e.g. number average molecular weight of from about 200 to about 400). Preferred are the acrylamides, methacrylamides, and cinamides. Especially preferred are the acrylamides and methacrylamides.

Grafted to the backbone of the copolymers hereof will be a plurality silicone macromer having a weight average molecular weight of at least about 500, preferably from about 1,000 to about 100,000, more preferably from about 2,000 to about 50,000, most preferably from about 5,000 to about 20,000.

The silicone-grafted polymers are such that when formulated into the finished hair care composition, and dried, the polymer phase separates into a discontinuous phase which includes the silicone macromer portion and a continuous phase which includes the organic, non-silicone backbone portion.

The silicone macromer of the copolymers of the present invention are generally incorporated into the polymers by terpolymerizing silicone macromer-containing monomers with the nonionic quaternizable monomers and the nonionic nonquaternizable monomer. Such silicone macromer-containing monomers have the general formula:

$$X(Y)_n Si(R)_{3-m} Z_m$$

wherein X is a vinyl group copolymerizable with the other monomers of the polymer; Y is a divalent linking group; R is a hydroxyl, lower alkyl (e.g. $C_1$–$C_4$), aryl, alkylamino, alkaryl, hydrogen or alkoxy; Z is a monovalent siloxane polymeric moiety having a number average molecular weight of at least about 500, and is pendant from the organic polymeric backbone, described above; n is 0 or 1; and m is an integer from 1 to 3. Of course, Z should be essentially unreactive under polymerization conditions. The silicone-containing monomer preferably has a weight average molecular weight of at least about 1,000, preferably from about 1,000 to about 100,000, more preferably from about 2,000 to about 50,000, most preferably from about 5,000 to about 20,000. Preferably, it is of the formula:

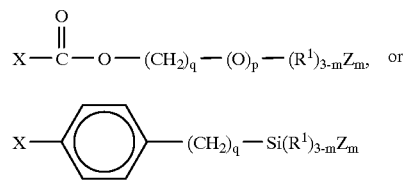

wherein m is 1, 2 or 3 (preferably m=1); p is 0 or 1, preferably 0; R is alkyl or hydrogen; q is an integer from 1 to 6; X is

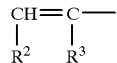

$R^2$ is hydrogen or —COOH (preferably $R^2$ is hydrogen); $R^3$ is hydrogen, methyl or —$CH_2COOH$ (preferably $R^3$ is methyl); Z is

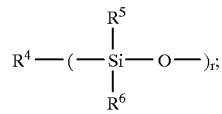

$R^4$, $R^5$, $R^6$ independently are alkyl, alkoxy, alkylamino, aryl, alkaryl, hydrogen, or hydroxyl (preferably alkyl, more preferably methyl); and r is an integer of at least about 5, preferably from about 10 to about 1500, (more preferably from about 25 to about 700); most preferably from about 70 to about 250.

The silicone-containing monomers of the polymers hereof can be polymerized in a silicone-containing monomer form. Alternatively, they can be polymerized in the form of their non-silicone containing precursor, and a silicone group can then be added. For example, carboxylate-containing monomers, such as acrylic acid, can be polymerized and then reacted with a silicone-containing compound with a terminal epoxy group. The result will, in general, be a silicone-containing monomer in the polymer having an equivalent structure to the formula $X(Y)_n Si(R)_{3-m} Z_m$, described above, and is intended to be encompassed herein.

Examples of synthesis of silicone macromer-containing copolymers are described in detail in U.S. Pat. No. 4,693,935, Mazurek, issued Sep. 15, 1987, and U.S. Pat. No. 4,728,571, Clemens et al., issued Mar. 1, 1988, both of which are incorporated herein by reference, and also in U.S. Pat. No. 5,061,481, Suzuki et al., issued Oct. 29, 1991, U.S. Pat. No. 5,219,560, Suzuki et al., issued Jun. 15, 1993, U.S. Pat. No. 5,166,276, Hayama et al., issued Nov. 24, 1992, U.S. Pat. No. 5,106,609, Bolich et al., issued Apr. 21, 1992, U.S. Pat. No. 5,100,658, Bolich et al., issued Mar. 31, 1992, U.S. Pat. No. 5,100,657, Ansher-Jackson et al., issued Mar. 31, 1992, U.S. Pat. No. 5,104,646, Bolich et al., issued Apr. 14, 1992, EPO 0 412 707, Torgerson et al., granted Feb. 4, 1994, EPO 0 412 704, Bolich et al., published Feb. 13, 1991, EPO application 92918969.4, Peffly, filed Aug. 18, 1992, EPO Application 92918839.9, Hozshuh, et al., filed Aug. 18, 1992, and EPO Application 92919224.3, filed Aug. 18, 1992, all of which are incorporated herein by reference.

The polymers hereof can also contain nonionic, non-water soluble monomers as optional ingredients, in amounts such that the polymer, as a whole, remains soluble in water. In general, it is preferred for the content of such optional monomers be no greater than about 20% by weight of the copolymer, more preferably no greater than about 10%, most preferably 0% or no greater than about 5%. It is also preferred for the polymers to be free of anionic monomers, which can interact with the cationic functionalities of the polymers and result in precipitation out of solution. If present, anionic monomers should be limited to a low level, such as about 5% or less, preferably 0% to no more than about 1%.

Representative examples of nonionic, non-water soluble monomers are acrylic or methacrylic acid esters of $C_1$–$C_{18}$ alcohols such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, and the like, the alcohols having from about 1–24 carbon atoms with the average number of carbon atoms preferably being from about 4–18, more preferably from about 4–12; styrene; chlorostyrene; vinyl esters such as vinyl acetate; vinyl chloride; vinylidene chloride; acrylonitrile; alpha-methylstyrene; t-butylstyrene; butadiene; cyclohexadiene; ethylene; propylene; vinyl toluene; alkoxyalkyl (meth)acrylate, such as methoxy ethyl (meth)acrylate and butoxyethyl (meth)acrylate; and mixtures thereof. Other nonionic monomers include acrylate and methacrylate derivatives such as allyl acrylate and methacrylate, cyclohexyl acrylate and methacrylate, and methacrylate, oleyl acrylate and methacrylate, benzyl acrylate and methacrylate, tetrahydrofurfuryl acrylate and methacrylate.

The polymers are synthesized by free radical polymerization methods, the general principles of which are well understood. See, for example, Odian, "Principles of Polymerization", 2nd edition, John Wiley & Sons, 1981, pp. 179–318. The desired monomers are all placed in a reactor, along with a sufficient amount of a mutual, polar, water-miscible solvent so that when the reaction is complete the viscosity of the reaction is reasonable. Suitable solvents include acteone, ethanol, and tetrahydrofuran. Typical monomer loadings are from about 20% to about 50%. Undesired terminators, especially oxygen, are removed as needed. This is done by evacuation or by purging with an inert gas, such as argon or nitrogen. The initiator is introduced and the reaction brought to the temperature needed for initiation to occur, assuming thermal initiators are used. Alternatively, redox or radiation initiation can be used as desired. The polymerization is allowed to proceed as long as needed for a high level of conversion to be achieved, typically from a few hours to a few days. The solvent is then removed, usually by evaporation or by precipitating the polymer by addition of a nonsolvent. The polymer is further purified, as needed.

Subsequent to polymerization, the polymer can be quaternized to the degree desired by conventional quaternization reactions, such as those described above.

By way of example, Polymers I, II and III, described above, are synthesized in the following manner. There are numerous variations on these procedures which are entirely up to the discretion of the synthetic chemist (e.g., choice of degassing method and gas, choice of initiator type, extent of conversion, reaction loading, etc.). The choice of initiator and solvent are often determined by the requirements of the particular monomers used, since different monomers have different solubilities and different reactivities to a specific initiator.

Polymer I

Place 30 parts dimethylaminopropyl methacrylamide, 55 parts isopropyl acrylamide, and 15 parts 15,000 wt. average molecular weight (15K) polydimethylsiloxane (PDMS) macromer in a flask. Add sufficient acetone to produce a final monomer concentration of 20%. Add initiator, azobisisobutyronitrile (AIBN), to a level of 0.5% by weight relative to the amount of monomer. Evacuate the vessel, and refill with nitrogen. Heat to 60° C. and maintain this temperature for 20 hours while agitating. Terminate the reaction by cooling to room temperature, and dry off the acetone by pouring the reaction mixture into a teflon-coated pan and placing in a vacuum oven.

For quaternization, place polymer in a flask equiped with a magnetic stirrer. Add sufficient quanitity of ethanol to produce a final polymer concentration of 20%, by weight. Add a 14.8 g diethylsulfate per 50.0 g polymer (or other desired stochiometric quantity, relative to the degree of quaternization desired) for 100% quaternization of quaternizable monomer dropwise to the flask, continue stirring for two hours. Evaporate the ethanol to obtain the quaternized copolymer.

Polymer II

Place 30 parts dimethylaminopropylacrylamide, 55 parts isopropylacrylamide, and 15 parts 15K PDMS macromer in a reaction vessel fitted with a temperature probe, reflux condenser, inlet port, and argon sparge. Add sufficient acetone to bring the final monomer concentration to 20% by weight. Sparge with argon for 1 to 2 hours. While sparging, heat to 58° C. in a water bath. Add initiator, azobisisobutyronitrile, to a level of 0.5% by weight relative to the weight of monomer present. Maintain temperature at 58° C., with a sufficient rate of argon flow to keep the solution mixed. Terminate the reaction after 20 hours and purify as with Polymer I.

For quaternization, solubilize the polymer in sufficient ethanol to form a 20% solution. Bubble methyl chloride gas through the solution until the polymer begins to precipitate out of solution, for approximately 100% (theoretical) quaternization. Decant the solution and dry polymer. Reduce methyl chloride bubbling period for lower quaternization levels.

Polymer III

Place 30 parts dimethylaminoethylmethacrylate, 50 parts isopropylacrylamide, 10 parts 15K PDMS macromer in a reaction vessel fitted with an argon sparge, temperature probe, reflux condenser and inlet port. Add sufficient acetone to bring the final monomer concentration to 20% by weight. Begin stirring and sparge with argon for 1 hour. While sparging, heat to 58° C. in a water bath. Add initiator, azobisisobutyronitrile, to a level of 1.0% by weight relative to the weight of monomer present. Continue stirring and a slow argon sparge and maintain the reaction temperature at 58° C. Allow to react for 20 hours. Terminate the reaction and remove the solvent as with Polymer I.

For quaternization, solubilize the polymer in sufficient ethanol to form a 20% solution. Bubble methyl chloride gas through the solution until the polymer begins to precipitate out of solution, for approximately 100% (theoretical) quaternization. Decant the solution and dry polymer. Reduce methyl chloride bubbling period for lower quaternization levels.

Aqueous Carrier

The compositions of the present invention comprise from about 75% to about 99.9%, by weight, water, as a carrier for the silicone macromer grafted copolymer, preferably from about 85% to about 99%, more preferably from about 90% to about 99%.

The silicone macromer grafted copolymer hereof is soluble in the aqueous carrier. In view of this solubility, it is not necessary to include in the compositions, organic solvents (including volatile organic solvents) such as ethanol, silicone fluids such as cyclomethicone, or hydrocarbon solvents to aid in the solubilization of the copolymer. Accordingly, the compositions hereof are preferably substantially free of such solvents. By substantially free, what is meant is no more than about 10%, by weight, of such solvents preferably no more than about 5%, more preferably no more than about 1%, most preferably zero percent.

Hair Care Compositions

The compositions of the present invention can comprise a wide variety of additional ingredients for cosmetic, therapeutic, or rheology modifying purposes. Exemplary non-limiting additional ingredients are described below. The compositions of the present invention can be in the form of liquids, lotions, creams, gels, etc.

The carrier may include gel vehicle materials or other rheology modifiers. These are particularly contemplated for use in products such as hair rinses, shampoos, and creams and lotions.

Gel vehicles can comprise two essential components: a lipid vehicle material and a cationic surfactant vehicle material. Cationic surfactant materials are described in detail below. Gel vehicles are generally described in the following documents, all incorporated by reference herein: Barry, "The Self Bodying Action of the Mixed Emulsifier Sodium Dodecyl Sulfate/Cetyl Alcohol", 28 J. of Colloid and Interface Science 82–91 (1968); Barry, et al., "The Self-Bodying Action of Alkyltrimethylammonium Bromides/Cetostearyl Alcohol Mixed Emulsifiers; Influence of Quaternary Chain Length", 35 J. of Colloid and Interface Science 689–708 (1971); and Barry, et al., "Rheology of Systems Containing Cetomacrogol 1000—Cetostearyl Alcohol, I. Self Bodying Action", 38 J. of Colloid and Interface Science 616–625 (1972).

The carrier may incorporate one or more lipid vehicle materials, regardless of whether it also contains a cationic surfactant, which are essentially water-insoluble, and contain hydrophobic and hydrophilic moieties. Lipid vehicle materials include naturally or synthetically-derived acids, acid derivatives, alcohols, esters, ethers, ketones, and amides with carbon chains of from about 12 to about 22, preferably from about 16 to about 18, carbon atoms in length. Fatty alcohols and fatty esters are preferred; fatty alcohols are particularly preferred.

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

Lipid vehicle materials among those useful herein are disclosed in *Bailey's Industrial Oil and Fat Products*, (3rd edition, D. Swern, ed., 1979), incorporated by reference herein. Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, Villamarin, et al., issued May 26, 1981; British Specification 1,532,585, published Nov. 15, 1978; and Fuku Shima, et al., "The Effect of Cetostearyl Alcohol in Cosmetic Emulsions", 98 *Cosmetics & Toiletries* 89–112 (1983). Fatty esters included among those useful herein are disclosed in U.S. Pat. No. 3,341,465, Kaufman, et al., issued Sep. 12, 1976 (incorporated by reference herein). If included in the compositions of the present invention, the lipid vehicle material is typically present at from about 0.1% to about 10.0% of the composition; the cationic surfactant vehicle material is present at from about 0.05% to about 5.0% of the composition.

The use of nonionic cellulose ethers and water-soluble gums for thickening compositions are also contemplated. See for example, U.S. Pat. No. 4,557,928, Glover, issued Dec. 10, 1985, teaching a hair conditioner comprising a suspension system which consists of one of glucan gum, guar gum, and hydroxyethylcellulose; and U.S. Pat. No. 4,581,230, Grollier et al., issued Apr. 8, 1986, which teaches cosmetic compositions for treating hair which comprise as thickening agents hydroxyethylcellulose, or water-soluble vegetable thickening agents, such as guar gum, each incorporated herein by reference.

Cellulose ethers are relatively low molecular weight but which are capable of producing highly viscous aqueous solutions in practical concentrations. These materials are nonionic cellulose ethers having a sufficient degree of nonionic substitution selected from the group consisting of methyl, hydroxyethyl, and hydroxypropyl to cause them to be water-soluble and which are further substituted with a hydrocarbon radical having from about 10 to 24 carbon atoms in an amount between about 0.2 weight percent and the amount which renders said cellulose ether less than 1%, by weight, soluble in water. The cellulose ether to be modified is preferably one of low to medium molecular weight; i.e., less than about 800,000 and preferably between about 20,000 and 700,000 (about 75 to 2500 D.P.).

Nonionic water-soluble cellulose ethers are preferred polymers that can be employed in hair care compositions. Widely used, commercially-available nonionic cellulose ethers include methyl cellulose, hydroxy propyl methyl cellulose, hydroxyethyl cellulose, hydroxypropyl cellulose and ethyl hydroxyethyl cellulose.

Other carrier ingredients for use in the compositions of the present invention, especially for hair rinses, include combinations of hydrophobically-modified polymeric materials with surfactants, such as quaternary ammonium compounds (such as ditallowdimethyl ammonium chloride). These vehicles are described in detail in the following patents: U.S. Pat. No. 5,106,609, issued Apr. 21, 1992 to Bolich et al., U.S. Pat. No. 5,100,658, issued Mar. 31, 1992 to Bolich et al., U.S. Pat. No. 5,104,646, issued Apr. 14, 1992 to Bolich et al, and U.S. Pat. No. 5,100,657, issued Mar. 31, 1992 to Ansher-Jackson et al., each incorporated herein by reference.

These systems provide a gel-like rheology without necessarily being gels in the technical sense. By "hydrophobically modified nonionic water-soluble polymer" is meant a nonionic water-soluble polymer which has been modified by the substitution with a sufficient amount of hydrophobic groups to make the polymer less soluble in water. By "water-soluble" what is meant is the polymer or salt, thereof, constituting the polymer backbone of the thickener should be sufficiently soluble such that it forms a substantially clear solution when dissolved in water at a level of 1%, by weight of the solution, at 25° C. Hence, the polymer backbone of the primary thickener can be essentially any water-soluble polymer. The hydrophobic groups can be $C_8$ to $C_{22}$ alkyl, aryl alkyl, alkyl aryl groups and mixtures thereof. The degree of hydrophobic substitution on the polymer backbone should be from about 0.10% to about 1.0%, depending on the particular polymer backbone. More generally, the ratio of hydrophilic portion to hydrophobic portion of the polymer is from about 10:1 to about 1000:1.

Nonionic water-soluble cellulose ethers are preferred to be employed as the polymer substrate of these hydrophobically modified polymers. Thus, e.g., hydroxyethyl cellulose, hydroxypropyl cellulose, methyl cellulose, hydroxypropyl methyl cellulose, ethyl hydroxyethyl cellulose, and methyl hydroxyethyl cellulose can all be modified. The amount of nonionic substituent such as methyl, hydroxyethyl or hydroxypropyl is taught not to be critical so long as there is an amount sufficient to assure that the ether is water-soluble.

The long chain alkyl modifier can be attached to the cellulose ether substrate via an ether, ester or urethane linkage. The ether linkage is preferred.

One commercially available material which meets these requirements is NATROSOL PLUS Grade 430, hydrophobically modified hydroxyethylcellulose available from Aqualon Company, Wilmington, Del. This material has a $C_{16}$ alkyl substitution of about 0.5% to about 0.9% by weight. The hydroxyethyl molar substitution for this material is from about 2.8 to about 3.2. The average molecular weight for the water-soluble cellulose prior to modification is approximately 300,000.

Another material of this type is sold under the trade name NATROSOL PLUS CS Grade D-67, by Aqualon Company, Wilmington, Del. This material has a $C_{16}$ alkyl substitution of from about 0.50% to about 0.95%, by weight. The hydroxyethyl molar substitution for this material is from about 2.3 to about 3.3. The average molecular weight for the water-soluble cellulose prior to modification is approximately 700,000.

Examples of water soluble polymers include hydroxyethylcellulose, hydroxypropyl cellulose, hydroxypropyl methylcellulose, polyethylene glycol, polyacrylamide, polyacrylic acid, polyvinyl alcohol, polyvinyl pyrrolidone, dextrans, for example Dextran purified crude Grade 2P, available from D&O Chemicals, plant exudates such as acacia, ghatti, and tragacanth, seaweed extracts such as sodium alginate, propylene glycol alginate, sodium carrageenan, cationic polymers such as Ucare JR-polymer (a cationic modified hydroxyethyl cellulose available from Union Carbide), natural polysaccharide materials, such as guar gum, locust bean gum, and xanthan gum.

When such systems are used to thicken the present compositions, from about 0.3% to about 5.0%, preferably from about 0.4% to about 3.0%, of the hydrophobically modified nonionic polymer is preferably utilized with from about 0.3% to about 5.0%, preferably from about 0.4% to about 3.0%, of the water-soluble polymeric material.

An alternative secondary thickening material for the hydrophobically modified nonionic polymer is a water-soluble surfactant having a molecular weight of less than about 20,000. By "water-soluble surfactant" is meant surfactant materials which form substantially clear, isotropic solutions when dissolved in water at 0.2 weight percent at 25° C.

Essentially any water-soluble surfactant material which meets these requirements will work in the present invention, including the following exemplary materials: cetyl betaine, ammonium lauryl sulfate, ammonium laureth sulfate, cetyl trimethyl ammonium chloride, and mixtures thereof.

When such systems are used to thicken the present compositions, from about 0.1% to about 10.0%, preferably from about 0.2% to about 5.0%, of the hydrophobically-modified nonionic water soluble polymer is generally utilized with from about 0.02% to about 0.30%, preferably from about 0.05% to about 0.30%, most preferably from about 0.05% to about 0.20%, of the water-soluble surfactant. The water-soluble surfactant level is kept low because higher levels of water-soluble surfactants interfere with the hydrophobically-modified hydroxyethyl cellulose thickener and produce compositions with much less desirable rheologies.

When the hydrophobically-modified polymer is combined with is a water-insoluble surfactant having a molecular weight of less than about 20,000. By "water-insoluble surfactant" is meant surfactant materials which do not form substantially clear isotropic solutions when dissolved in water at greater than 0.2 weight percent at 25° C.

Essentially any water-insoluble surfactant material which meets these requirements will work in the present invention, however, water-insoluble cationic surfactant materials are preferred. Cationic surfactants are further described below. The following nonexclusive surfactant materials are suitable: stearamide diethanolamine (stearamide DEA), cocoamide methanolamine (cocoamide MEA), dimethyl stearamine oxide, glyceryl monooleate, sucrose stearate, PEG-2 stearamine, polyethylene glycol ethers of fatty alcohols, such as Ceteth-2 of the formula $CH_3$—$(CH2)14$-$CH2$-$(OCH2CH2)_n$—OH, where n has an average value of 2 (commercially available under the trade name Brij 56 from ICI Americas), glycerol stearate citrate, dihydrogenated tallow dimethyl ammonium chloride, polyoxyethylene, polyoxypropylene block polymers such as Poloxamer 181, of the formula:

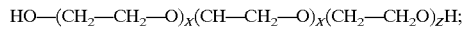

$HO$—$(CH_2$—$CH_2$—$O)_x(CH$—$CH_2$—$O)_x(CH_2$—$CH_2O)_zH$;

wherein on average x=3, y=30 and z=3 (commercially available from BASF Wyandotte under the trade name Pluronic L-61), hydrogenated tallow dimethyl betaine, and hydrogenated tallow amide DEA.

When such systems are used to thicken the present compositions, from about 0.1% to about 10.0%, preferably from about 0.2% to about 5.0%, of the hydrophobically-modified hydroxyethyl cellulose is generally utilized with from about 0.02% to about 10.0%, preferably from about 0.05% to about 3.0%, most preferably from about 0.05% to about 2.0%, of the water-insoluble surfactant.

It is also contemplated to utilize a suspending agent to thicken the compositions and/or suspend the polymer/resin/solvent phase. Suitable suspending agents are long chain acyl derivatives, long chain amine oxides, and mixtures thereof, wherein such suspending agents are present in the shampoo compositions in crystalline form. A variety of such suspending agents are described in U.S. Pat. No. Reissue 34,584, Grote et al., issued Apr. 12, 1994. Especially preferred is ethylene glycol distearate.

Also included among the long chain acyl derivatives useful as suspending agents are the N,N-di(hydrogenated) $C_8$–$C_{22}$ (preferably $C_{12}$–$C_{22}$, more preferably $C_{16}$–$C_{18}$) amido benzoic acid, or soluble salt (e.g., K, Na salts) thereof particularly N,N-di(hydrogenated)tallow amido benzoic acid which is commercially marketed by Stepan Company (Northfield, Ill., USA).

Surfactants are optional ingredients in the compositions of the invention. When present, the surfactant typically comprises from about 0.05% to about 50% of the composition. Surfactants useful in compositions of the present invention include anionic, nonionic, cationic, and amphoteric surfactants. For a shampoo, the level is preferably from about 5% to about 30%, most preferably from about 10% to about 25%, of the composition. For conditioners, the preferred level of surfactant is from about 0.1% to about 3%. Mousses are particularly preferred compositions of the present invention. Mousses will generally comprise a foaming agent, such as an amine oxide, especially $C_{10}$–$C_{22}$ alkyl amine oxides, preferably $C_{12}$–$C_{18}$, a sufractant especially an amphoteric surfactant such as a betaine, or a combination thereof. Such foaming agents will generally be used at a level of from about 0.05% to about 3%, preferably from about 0.1% to about 2%.

Synthetic anionic detergents useful herein, particularly for shampoo compositions, include alkyl and alkyl ether sulfates. These materials typically have the respective formulae $ROSO_3M$ and $RO(C_2H_4O)xSO_3M$, wherein R is alkyl or alkenyl of from about 10 to about 20 carbon atoms, x is 1 to 10, and M is a water-soluble cation such as ammonium, sodium, potassium and triethanolamine.

Another suitable class of anionic surfactants are the water-soluble salts of the organic, sulfuric acid reaction products of the general formula:

wherein $R_1$ is chosen from the group consisting of a straight or branched chain, saturated aliphatic hydrocarbon radical having from about 8 to about 24, preferably about 12 to about 18, carbon atoms; and M is a cation. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12-18}$ n-paraffins.

Additional examples of anionic synthetic surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic surfactants of this variety are set forth in U.S. Pat. Nos. 2,486,921; 2,486,922; and 2,396,278.

Still other anionic synthetic surfactants include the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuc cinicacid; dioctyl esters of sodium sulfosuccinic acid.

Other suitable anionic surfactants utilizable herein are olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The α-olefins from which the olefin sulfonates are derived are mono-olefins having about 12 to about 24 carbon atoms, preferably about 14 to about 16 carbon atoms. Another class of anionic organic surfactants are the β-alkyloxy alkane sulfonates. These compounds have the following formula:

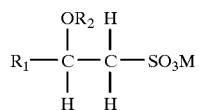

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Many additional nonsoap synthetic anionic surfactants are described in *McCutcheon's, Detergents and Emulsifiers,* 1984 *Annual,* published by Allured Publishing Corporation, which is incorporated herein by reference. Also U.S. Pat. No. 3,929,678, Laughlin et al., issued Dec. 30, 1975, discloses many other anionic as well as other surfactant types and is incorporated herein by reference. Soaps can also be utilized as anionic surfactants.

Nonionic surfactants, can be broadly defined as compounds produced by the condensation of alkylene oxide groups (hydrophilic in nature) with an organic hydrophobic compound, which may be aliphatic or alkyl aromatic in nature. Examples of classes of nonionic surfactants are:

1. Those derived from the condensation of ethylene oxide with the product resulting from the reaction of propylene oxide and ethylene diamine products.

2. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

3. Long chain tertiary amine oxides such as those corresponding to the following general formula:

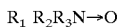

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals (the arrow in the formula is a conventional representation of a semipolar bond).

4. Long chain tertiary phosphine oxides corresponding to the following general formula:

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond.

5. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetra decyl methyl sulfoxide, 3-methoxytridecyl methyl sulfoxide, 3-hydroxytridecyl methyl sulfoxide, 3-hydroxy-4-dodecoxybutyl methyl sulfoxide.

Cationic surfactants useful in compositions of the present invention, particularly the conditioner compositions, contain amino or quaternary ammonium hydrophilic moieties which are positively charged when dissolved in the aqueous composition of the present invention. Cationic surfactants among those useful herein are disclosed in the following documents, all incorporated by reference herein: M. C. Publishing Co., *McCutcheon's, Detergents & Emulsifiers*, (North American edition 1979); Schwartz, et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983. If included in the compositions of the present invention, the cationic surfactant is generally resent at from about 0.05% to about 5%.

Among the quaternary ammonium-containing cationic surfactant materials useful herein are those of the general formula:

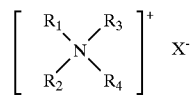

wherein $R_1$–$R_4$ are independently an aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups. The longer chain aliphatic groups, e.g., those of about 12 carbons, or higher, can be saturated or unsaturated.

Other quaternary ammonium salts useful herein are diquaternary ammonium salts, such as tallow propane diammonium dichloride.

Quaternary ammonium salts include dialkyldimethylammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieocosyol dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(saturated or unsaturated tallow) dimethyl ammonium chloride is a particularly preferred quaternary ammonium salt.

Salts of primary, secondary and tertiary fatty amines are also suitable cationic surfactant materials. The alkyl groups of such amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

Amphoteric surfactants, include those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic water-solubilizing group, e.g., carboxy, sulfonate, sulfate, phosphate, or phosphonate. A general formula for these compounds is:

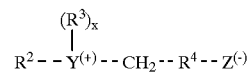

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other amphoterics such as betaines are also useful in the present invention. Examples of betaines useful herein include the high alkyl betaines, such as coco dimethyl carboxymethyl betaine, lauryl dimethyl carboxymethyl betaine, lauryl dimethyl alpha carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH($CH_2$)$_3$ radical is attached to the nitrogen atom of the betaine are also useful in this invention.

Other examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylamino propane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Silicone Hair Conditioning Agent

An optional component of the present invention is a nonvolatile, silicone conditioning agent.

The silicone hair conditioning agent for use herein will preferably have an average viscosity of from about 1,000 to about 2,000,000 centistokes at 25° C., more preferably from about 10,000 to about 1,800,000, even more preferably from about 100,000 to about 1,500,000. The viscosity of silicones herein can, in general, be measured by means of a glass capillary viscometer as set forth in Dow Corning Corporate Test Method CTM0004, Jul. 20, 1970.

The silicone hair conditioning agent will typically be used in the shampoo compositions hereof at levels of from about 0.05% to about 10% by weight of the composition, preferably from about 0.1% to about 10%, more preferably from about 0.5% to about 8%, most preferably from about 0.5% to about 5%.

Suitable insoluble, nonvolatile silicone fluids include polyalkyl siloxanes, polyaryl siloxanes, polyalkylaryl siloxanes, polyether siloxane copolymers, and mixtures thereof. Other insoluble, nonvolatile silicone fluids having hair conditioning properties can also be used. The term "nonvolatile" as used herein shall mean that the silicone material exhibits very low or no significant vapor pressure at ambient conditions, as is understood by those in the art. In general, this will mean no more than 0.2 mm Hg at one atomosphere and 25° C. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000.

Silicone fluids hereof include polyalkyl or polyaryl siloxanes with the following structure:

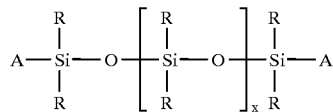

wherein R is alkyl or aryl, and x is an integer from about 1 to about 8,000 may be used, preferably from about 5 to about 8,000. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

The nonvolatile polyalkylsiloxane fluids that may be used include, for example, polydimethylsiloxanes. These siloxanes are available, for example, from the General Electric Company in their Viscasil® and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Another silicone material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

Cationic Polymer Hair Conditioning Agent

The compositions of the present invention can also comprise a water soluble, cationic organic polymer conditioning agent for hair. The polymeric cationic conditioning agent hereof will generally be present at levels of from about 0.05% to about 5%, preferably from about 0.1% to about 4%, more preferably from about 0.2% to about 3%, by weight, of the shampoo composition. By "water soluble" cationic organic polymer, what is meant is a polymer which is sufficiently soluble in water to form a substantially clear solution to the naked eye at a concentration of 0.1% in water (distilled or equivalent) at 25° C. Preferably, the polymer will be sufficiently soluble to form a substantially clear solution at 0.5% concentration, more preferably at 1.0% concentration.

The cationic organic polymers useful in the hair conditioning agent hereof are organic polymers that can provide conditioning benefits to hair and that are soluble in the shampoo composition. Any cationic polymers which can provide these benefits can be used. As used herein, the term "polymer" shall include materials whether made by polymerization of one type of monomer or made by two (i.e., copolymers) or more types of monomers.

The cationic polymers hereof will generally have a weight average molecular weight which is at least about 5,000, typically at least about 10,000, and is less than about 10 million. Preferably, the molecular weight is from about 100,000 to about 2 million. The cationic polymers will have cationic nitrogen-containing moieties such as quaternary ammonium or cationic amino moieties, or a mixture thereof.

Any anionic counterions can be utilized for the cationic polymers so long as the water solubility criteria is met. Suitable counterions include halides (e.g., Cl—, Br—, I—, or F—, preferably Cl—, Br—, or I—), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the shampoo. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives.

Cationic polysaccharide polymer materials suitable for use herein include those of the formula:

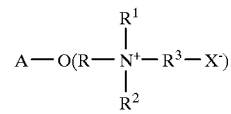

wherein:

A is an anhydroglucose residual group, such as a starch or cellulose anhydroglucose residual, R is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Cationic cellulose is available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted opoxide, referred to in the industry (CTFA) as Polyquaternium 24. These materials are available from Amerchol Corp. (Edison, N.J., USA) under the tradename Polymer LM-200.

Other cationic polymers that can be used include cationic guar gum derivatives, such as guar hydroxypropyltrimonium chloride (commercially available from Celanese Corp. in their Jaguar® series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein).

Organic Oil Conditioning Agents

The compositions of the present invention can also comprise a nonvolatile, water insoluble, organic, oil as a conditioning agent for hair. The hair conditioning oily liquid can add shine and luster to the hair. The conditioning oil is typically present in the compositions at a level of from about 0.05% to about 5%, by weight of the composition, preferably from about 0.2% to about 3%, more preferably from about 0.5% to about 1%.

By "nonvolatile" what is meant is that the oily material exhibits very low or no significant vapor pressure at ambient conditions (e.g., 1 atmosphere, 25° C.), as is understood in the art. The nonvolatile oily materials preferably have a boiling point at ambient pressure of about 250° C. or higher.

By "water insoluble" what is meant is that the oily liquid is not soluble in water (distilled or equivalent) at a concentration of 0.1%, at 25° C.

The conditioning oil hereof generally will have a viscosity of about 3 million cs or less, preferably about 2 million cs or less, more preferably about 1.5 million cs or less.

The conditioning oils hereof are liquids selected from the group consisting of hydrocarbon oils and fatty esters. The fatty esters hereof are characterized by having at least 10 carbon atoms, and include esters with hydrocarbyl chains derived from fatty acids or alcohols, e.g., mono-esters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g., ethoxy or ether linkages, etc.).

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 19 carbon atoms, although it is not necessarily meant to be limit the hydrocarbons to this range. Branched chain hydrocarbon oils can and typically may contain higher numbers of carbon atoms. Also encompassed herein are polymeric hydrocarbons of alkenyl monomers, such as $C_2$–$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 500, preferably from about 200 to about 400, more preferably from about 300 to about 350. Specific examples of suitable materials include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, sold by Permethyl Corporation. A preferred hydrocarbon polymer is polybutene, such as the copolymer of isobutylene and butene. A commercially available material of this type is L-14 polybutene from Amoco Chemical Co. (Chicago, Ill., U.S.A.).

Monocarboxylic acid esters hereof include esters of alcohols and/or acids of the formula R'COOR wherein alkyl or alkenyl radicals and the sum of carbon atoms in R' and R is at least 10, preferably at least 20.

Fatty esters include, for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

The mono-carboxylic acid ester however need not necessarily contain at least one chain with at least 10 carbon atoms, so long as the total number of aliphatic chain carbon atoms is at least 10. Examples include diisopropyl adipate, diisohexyl adipate, and diisopropyl sebacate.

Di- and tri-alkyl and alkenyl esters of carboxylic acids can also be used. These include, for example, esters of $C_4$–$C_8$ dicarboxylic acids such as $C_1$–$C_{22}$ esters (preferably $C_1$–$C_6$) of succinic acid, glutaric acid, adipic acid, hexanoic acid, heptanoic acid, and octanoic acid. Specific examples include isocetyl stearyol stearate, diisopropyl adipate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters for use herein.

Glycerides include mono-, di-, and tri-glycerides. More specifically, included are the mono-, di-, and tri-esters of glycerol and long chain carboxylic acids, such as $C_{10}$–$C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include triolein and tristearin glyceryl dilaurate. Preferred glycerides are di-, and tri-glycerides. Especially preferred are triglycerides.

The compositions herein can contain a variety of other optional components suitable for rendering such compositions more cosmetically or aesthetically acceptable or to provide them with additional usage benefits, e. g. medicinal benefits. Such conventional optional ingredients are well-known to those skilled in the art, e.g., sunscreens, medicaments (e.g. anti-bacterials, anti-inflamatories, anti-acne actives, etc.), colors and dyes, perfumes, pearlescent aids, such as ethylene glycol distearate; preservatives, such as benzyl alcohol, methyl paraben, propyl paraben and imidazolidinyl urea; thickeners and viscosity modifiers, such as a diethanolamide of a long chain fatty acid (e.g., PEG 3 lauric diethanolamide), cocomonoethanol amide, dimethicone copolyols, guar gum, methyl cellulose, starches and starch derivatives; fatty alcohols, such as cetearyl alcohol; sodium chloride; sodium sulfate; polyvinyl alcohol; ethyl alcohol; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents, such as the thioglycolates; perfumes; sequestering agents, such as disodium ethylenediamine tetraacetate; and polymer plasticizing agents, such as glycerin, disobutyl adipate, butyl stearate, and propylene glycol. Such optional ingredients generally are used individually at levels of from about 0.01% to about 10.0%, preferably from about 0.05% to about 5.0%, of the composition.

The pH of the present compositions generally will be between about 3 and about 9, preferably between about 4 and about 8.

Compositions of the present invention can be dispensed from containers which are aerosol dispensers or pump spray dispensers. Such dispensers, i.e., containers, are well known to those skilled in the art and are commercially available from a variety of manufacturers, including American National Can Corp. and Continental Can Corp.

When the spray compositions are to be dispensed from a pressurized aerosol container, a propellant which consists of one or more of the conventionally-known aerosol propellants may be used to propel the compositions. A suitable propellant for use can be generally any liquifiable gas conventionally used for aerosol containers.

Suitable propellants for use are volatile hydrocarbon propellants which can include liquified lower hydrocarbons of 3 to 4 carbon atoms such as propane, butane and isobutane. Other suitable propellants are hydrofluorocarbons such as 1,2-difluoroethane (Hydrofluorocarbon 152A) supplied as Dymel 152A by DuPont. Other examples of propellants are dimethylether, nitrogen, carbon dioxide, nitrous oxide and atmospheric gas.

The aerosol propellant may be mixed with the present compositions or it may be contained in a separate phase or compartment of an aerosol container. The amount of propellant to be mixed is governed by normal factors well known in the aerosol art. The levels of the required and other optional composition ingredients described above are based upon the total weight of the hair care composition ingredients, and do not include aerosol propellants. Generally, for liquifiable propellants, the level of propellant is from about 3% to about 60% by weight of the total composition (hair care compositions and aerosol propellant), preferably from about 3% to about 50% by weight of the total composition.

Alternatively, pressurized aerosol dispensers can be used where the propellant is separated from contact with the hair spray composition such as a two compartment can of the type sold under the tradename SEPRO from Americal National Can Corp.

Other suitable aerosol dispensers are those characterized by the propellant being compressed air which can be filled into the dispenser by means of a pump or equivalent device prior to use. Such dispensers are described in U.S. Pat. Nos. 4,077,441, Mar. 7, 1978, Olofsson and 4,850,577, Jul. 25, 1989, TerStege, both incorporated by reference herein, and in U.S. Ser. No. 07/839,648, Gosselin et al., filed Feb. 21, 1992, also incorporated by reference herein. Compressed air aerosol containers suitable for use are also currently marketed by The Procter & Gamble Company under their tradename VIDAL SASSOON AIRSPRAY® hair sprays.

Conventional non-aerosol pump spray dispensers, i.e., atomizers, can also be used.

As with all compositions, the present invention should not contain components which unduly interfere with the performance of the compositions.

The hair care compositions of the present invention can be made using conventional formulation and mixing techniques. In general, the silicone grafted copolymer can be mixed with water prior to, simultaneously with, or subsequent to the addition of other, optional ingredients. The compositions are preferably heated to about 40° C.–60° C. with stirring and then allowed to cool for about six to eight hours to ambient temperature, with stirring.

Method of Using Hair Care Compositions

The hair care compositions of the present invention are used in conventional ways to provide the desired benefit appropriate to the product such as hair styling, holding, cleansing, conditioning and the like for hair care compositions. Such methods of use depend upon the type of composition employed but generally involve application of an effective amount of the product to the hair, which may then be rinsed from the hair (as in the case of shampoos and some conditioning products) or allowed to remain on the hair (as in the case of spray, mousse, or gel products). By "effective amount" is meant an amount sufficient to provide the benefit desired. Preferably, hair rinse, mousse, and gel products are applied to wet or damp hair prior to drying and styling of the hair. After such compositions are applied to the hair, the hair is dried and styled in the usual ways of the user. Hair sprays are typically applied to dry hair after it has already been dried and styled.

The present compositions can also be used for topical application to the skin and in cosmetic and topical health care compositions, and such uses thereof are not necessarily meant to be excluded from the claims below unless otherwise provided.

The following examples further illustrate preferred embodiments within the scope of the present invention. The examples are given solely for the purposes of illustration and are not to be construed as limitations of the present invention as many variations of the invention are possible without departing from its spirit and scope.

EXAMPLES 1–4

Disclosed below are exemplary mousse compositions of the present invention.

| Component (wt. %) | 1 | 2 | 3 | 4 |
|---|---|---|---|---|
| Silicone Grafted Copolymer[1] | 3.00 | 3.00 | 3.00 | 3.00 |
| Lauramine-oxide | 0.10 | 0.10 | 0.00 | 0.10 |
| Cocamidopropyl betaine | 1.33 | 1.33 | 0.30 | 1.33 |
| Propylene glycol | 0.20 | 0.10 | 0.10 | 0.10 |
| Perfume | 0.10 | 0.10 | 0.05 | 0.10 |

-continued

| Component (wt. %) | 1 | 2 | 3 | 4 |
| --- | --- | --- | --- | --- |
| Disodium EDTA - dihydrate | 0.10 | 0.10 | 0.10 | 0.10 |
| Phenoxyethanol | 0.25 | 0.25 | 0.25 | 0.25 |
| Methyl paraben | 0.15 | 0.15 | 0.15 | 0.15 |
| Polyquaternium-4[2] | 0.00 | 0.00 | 0.00 | 0.20 |
| Stearyltrimethylammonium chloride | 0.00 | 0.00 | 0.20 | 0.00 |
| Deionized Water | q.s. | q.s. | q.s. | q.s. |

[1]Polymer I, II, or III, described above.
[2]Celquat L200, National Starch and Chemical Corp. (Bridgewater, NJ, USA, copolymer of hydroxyethylcellulose and diallyldimethyl ammonium chloride.

The composition is made by mixing the silicone grafted copolymer in the water, sequentially adding the ramaining ingredients, except for perfume, with stirring, heating to 40° C.–60° C. with stirring and, stirring for about eight hours while allowing the composition to cool at ambient temperature, and then mixing in the perfume. The product can then be packaged in a conventional aerosol or non aerosol mousse spray package.

EXAMPLES 5–8

Below are several exemplary hair spray compositions of the present invention.

| Component (wt. %) | 5 | 6 | 7 | 8 |
| --- | --- | --- | --- | --- |
| Silicone Grafted Copolymer[1] | 5.00 | 5.00 | 5.00 | 5.00 |
| Perfume | 0.10 | 0.10 | 0.10 | 0.10 |
| Deionized Water | q.s. | q.s. | q.s. | q.s. |

The compositions are made by mixing the silicone grafted copolymer in the water, heating to 40° C.–60° C. with stirring and cooling to ambient temperature, stirring for about eight hours while allowing the composition to cool.

EXAMPLE 9

The following is a shampoo composition representative of the present invention.

| Component | Weight % |
| --- | --- |
| Ammonium laureth sulfate | 5.00 |
| Cocamido propyl betaine | 6.00 |
| Silicone Grafted Copolymer I, II, III | 2.00 |
| PEG 150 distearate | 2.00 |
| Glydant[1] | 0.38 |
| Perfume | 1.00 |
| Deionized Water | q.s. |

[1]Preservative commercially available from Glyco, Inc.

The shampoo is prepared by combining the ammonium laureth sulfate (normally supplied as a 28% solution in water) and Silicone Grafted Copolymer and heating to 70° C. for about ½ hour with mixing. The remaining ingredients are added and mixed for an additional ½ hour. The batch is then cooled to ambient temperature. Composition pH is adjusted to 6.5 by the addition of citric acid or sodium hydroxide, if necessary.

EXAMPLE 10

The following is a styling rinse composition representative of the present invention.

| Component | Weight % |
| --- | --- |
| Silicone Grafted Copolymer I, II, III Premix | 3.00 |
| Silicone Gum GE SE76[1] | 0.50 |
| Decamethyl cyclopentasiloxane | 4.00 |
| Main Mix | |
| Cetyl hydroxyethylcellulose[2] | 0.60 |
| Locust bean gum | 0.50 |
| EDTA, disodium salt | 0.15 |
| DTDMAC | 0.65 |
| Glydant[3] | 0.40 |
| Deionized Water | q.s. |

[1]Commercially available from General Electric
[2]Polysurf from Aqualon Co.
[3]Preservative commercially available from Glyco, Inc.

The Premix is blended separately by conventional means. The Main Mix is prepared by adding all the ingredients and heating to 95° C. for ½ hour with agitation. As the batch is cooled to about 60° C., the Premix and Silicone Grafted Copolymer are added to the Main Mix with agitation and the batch is cooled to ambient temperature.

What is claimed is:

1. An aqueous hair setting composition, comprising:
   (a) from about 0.1% to about 15%, by weight, of a cationic, water soluble polymeric hair setting agent, said hair setting agent being a silicone macromer-grafted copolymer consisting essentially of:
      (i) from about 1% to about 20%, by weight, silicone macromers;
      (ii) from about 5% to about 75%, by weight, nonionic, quaternizable monomers; and
      (iii) from about 5% to about 90%, by weight, nonionic, water soluble, non-quaternizable monomers;
      wherein said copolymer has a degree of quaternization of at least about 5 wt. %, of the monomers, calculated by total weight of the copolymer, are quaternized and said copolymer has a backbone having a Tg of from about 30° C. to about 140° C.; and
   (b) from about 75% to about 99.9%, by weight, water.

2. An aqueous hair setting composition as in claim 1, wherein said composition is essentially free of volatile organic solvents.

3. An aqueous hair setting composition as in claim 2, wherein said polymer has a number average molecular weight of from about 10,000 to about 1,000,000.

4. An aqueous hair setting composition as in claim 3, wherein said monomers of element (a) (ii) are amino-functional ethylenically unsaturated monomers selected from the group consisting of amino-functional acrylamide, amino-functional methacrylamide, amino-functional $C_1$–$C_4$ alkyl acrylates, amino-functional $C_1$–$C_4$ alkyl methacrylates, amino-functional styrene, and combinations thereof.

5. An aqueous hair setting composition as in claim 3, wherein said monomers of element (a) (iii) are selected from the group consisting of acrylamide, methacrylamide, mono- and di-$C_1$–$C_6$ alkyl acrylamides, mono- and di-$C_1$–$C_6$ alkyl methacrylamides, cinamides, and combinations thereof.

6. An aqueous hair setting composition as in claim 4, wherein said monomers of element (a) (iii) are selected from the group consisting of acrylamide, methacrylamide, mono- and di-$C_1$–$C_6$ alkyl acrylamides, mono- and di-$C_1$–$C_6$ alkyl methacrylamides, cinamides, and combinations thereof.

7. An aqueous hair setting composition as in claim 5, wherein said monomers of element (a) (iii) are selected from the group consisting of $C_1$–$C_3$ mono- and di-alkyl acrylamides, acrylamide, methacrylamide, $C_1$–$C_3$ mono- and di-methacrylamides, and combinations thereof.

8. An aqueous hair setting composition as in claim 1, further comprising from about 0.05% to about 3%, by weight, of a foaming agent.

9. An aqueous hair setting composition as in claim 8, dispensed in an aerosol container, whereby said composition foams upon being dispensed.

10. An aqueous hair setting composition as in claim 1, comprising from about 2% to about 15% of said silicone macromer-containing monomer, from about 5 to about 60% of said quaternizable monomer, and from about 25% to about 70% of said nonquaternizable, nonionic monomer.

11. An aqueous hair setting composition as in claim 12, comprising from about 5% to about 10% of said silicone macromer-containing monomer, from about 5 to about 40% of said quaternizable monomer, and from about 30% to about 60% of said nonquaternizable, nonionic monomer.

12. An aqueous hair setting composition as in claim 1, wherein said copolymer is soluble in 10% dionized water at 25° C.

* * * * *